United States Patent
Hahr et al.

(10) Patent No.: US 9,889,039 B2
(45) Date of Patent: Feb. 13, 2018

(54) PENILE CONSTRICTION DEVICE

(71) Applicants: SENSES TOYS INTELLECTUAL PROPERTY MANAGEMENT UG, Bielefeld (DE); Meike Hahr, Hamburg (DE); Heiko Tullney, Hamburg (DE); Thomas Milewski, Halstenbek (DE)

(72) Inventors: Meike Hahr, Hamburg (DE); Heiko Tullney, Hamburg (DE); Thomas Milewski, Halstenbek (DE)

(73) Assignee: OVO JOINT VENTURE LLC, Hightstown, NJ (US)

( * ) Notice: Subject to any disclaimer, the term of this patent is extended or adjusted under 35 U.S.C. 154(b) by 0 days.

(21) Appl. No.: 14/345,348

(22) PCT Filed: Sep. 27, 2012

(86) PCT No.: PCT/EP2012/069155
§ 371 (c)(1),
(2) Date: Mar. 17, 2014

(87) PCT Pub. No.: WO2013/045595
PCT Pub. Date: Apr. 4, 2013

(65) Prior Publication Data
US 2015/0018610 A1    Jan. 15, 2015

Related U.S. Application Data

(63) Continuation of application No. PCT/EP2011/066931, filed on Sep. 28, 2011.

(51) Int. Cl.
*A61F 5/41* (2006.01)

(52) U.S. Cl.
CPC .......... *A61F 5/41* (2013.01); *A61F 2005/414* (2013.01); *A61F 2005/417* (2013.01)

(58) Field of Classification Search
CPC . A61F 5/41; A61F 2005/414; A61F 2005/417
(Continued)

(56) References Cited

U.S. PATENT DOCUMENTS 2,085,368 A * 6/1937 Kendall .................. 606/191
5,462,514 A * 10/1995 Harris ..................... A61F 5/41
600/38

(Continued)

FOREIGN PATENT DOCUMENTS

WO    WO2006056005    6/2006

OTHER PUBLICATIONS

International Search Report and Written Opinion dated Dec. 21, 2012 from PCT Application No. PCT/EP2012/069155, 8 pages.

*Primary Examiner* — Samuel Gilbert
(74) *Attorney, Agent, or Firm* — Richard E. Oney; Tiffany & Bosco, P.A.

(57) ABSTRACT

A penile constriction device has an elongated body with a coil-shaped portion and first and second end portions. In an operational mode, the end portions are biased into mutually overlapping positions and are longitudinally spaced apart. The coil-shaped portion is adapted to wrap closely around a penis. The coil-shaped portion of the elongated body includes an elongated elastic spring member. A head element is removably mounted to the first end portion of the elongated. The head element can be adapted to provide vibrations and light.

19 Claims, 2 Drawing Sheets

(58) Field of Classification Search
USPC .......................................... 600/38–41; 601/46
See application file for complete search history.

(56) References Cited

U.S. PATENT DOCUMENTS

| | | |
|---|---|---|
| 5,524,638 A | 6/1996 | Lyons |
| 5,873,813 A * | 2/1999 | Weiss ............................... 600/38 |
| 7,931,605 B2 * | 4/2011 | Murison ................ A61H 19/34 |
| | | 600/38 |
| 2005/0155609 A1 | 7/2005 | Lin |
| 2005/0203335 A1 * | 9/2005 | Stachon .......................... 600/39 |
| 2006/0063971 A1 * | 3/2006 | Hill ............................ A61F 5/41 |
| | | 600/38 |
| 2006/0178602 A1 * | 8/2006 | Teng ....................... A61H 19/34 |
| | | 601/70 |
| 2006/0241341 A1 | 10/2006 | Shelyakov et al. |
| 2009/0012355 A1 * | 1/2009 | Lin ........................ A61H 19/34 |
| | | 600/41 |

* cited by examiner

PENILE CONSTRICTION DEVICE

The present invention relates to a penile constriction device.

Penile constriction devices consisting generally of an elastic ring adapted to encircle the penis closely adjacent the base thereof and adjacent the user's body are known from the prior art. They act by constricting the flow of blood within the organ in a selective manner so that relatively easy flow of blood into the organ is permitted whereas the return flow of blood out of the organ into the body is restricted. This will result in erection of the organ in many cases, and is also effective in permitting longer retention of an erection once it has been obtained, wherein the penile constriction device will then be effective in retaining the erection as long as may be necessary.

However, penile constriction devices have in the past been subject to certain disadvantages. In particular, there is a problem to apply to and remove a penile constriction device from the organ, especially if the organ is already erected or partially erected.

It is an object of the present invention, to improve a penile constriction device for an easier and more convenient application to the organ.

In order to achieve the above and further objects, according to the present invention, there is provided a penile constriction device comprising an elongated body having elasticity and including first and second end portions, said elongated body being adapted to exhibit a ring shape in an operational mode, wherein the body is provided with such a shape and elasticity that in the operational mode both end portions are biased into mutually overlapping positions.

So, the device according to the present invention is not formed by a closed ring, but comprises an elongated body having first and second end portions. However, said first and second end portions are not permanently connected with each other. Rather, according to the present invention, the elongated body is provided with such a shape and elasticity that in the operational mode the elongated body exhibits a ring shape, but its both end portions are biased into mutually overlapping positions only, so that due to its biasing effect the elongated body wraps itself around the organ. So, the device according to the present invention wraps itself around the organ in order to apply sufficient force upon the organ and exhibits the function of a closed constriction ring in the operational mode, but there is always the option to open the elongated body for releasing the device from the organ by grabbing both end portions of the elongated and extending or spreading the elongated body. This is achieved by biasing both end portions into mutually overlapping positions without connecting with each other wherein the biasing force resulting from the elasticity is dimensioned so that the organ is subject to sufficient pressure on the one hand but the user is still able to apply a higher counterforce for compensation of said biasing force and, hence, opening of the elongated body on the other hand. After all, the present invention allows for an easy and convenient handling of the device along with the option to release the device from the organ whenever necessary.

Further advantageous embodiments and modifications of the present invention are defined in the dependent claims.

According to a preferred embodiment, the elongated body is provided with such a shape and elasticity that in the operational mode the body is biased so as to be twisted or to form at least a part of a coil or a helix. A coil or helix shape offers a tight and individually fitting to the organ.

According to a further preferred embodiment, the elongated body includes an elongated elastic spring member which is adapted to bias both end portions of the elongated body into mutually overlapping positions, wherein in particular the spring member may be adapted to bias the body into an at least partly twisted or helical or coil-shaped form. The provision of such an elongated elastic spring member is advantageous for wrapping the elongated body around the organ and achieving a tight and individual fitting shape under pressure.

A still further preferred embodiment comprises a head element, first coupling means provided at the head element, and second coupling means provided at a first end portion of the elongated body, said first and second coupling means being adapted to removably mount the head element to the first end portion of the elongated body. Due to the additional provision of a head element having a certain shape and/or function, the shape and/or function of the elongated body and, hence, of the whole device may be changed or even broadened, extended or increased. Since the coupling means are adapted to removably mount the head element to the first end portion of the elongated body, this embodiment offers the option to provide a plurality of different head elements having different shape and/or function among which the head element with the desired shape and/or function is selected for the current use, and hence to change the shape and/or function of the device by exchanging the head elements in accordance with the desired application.

According to an advantageous modification of the aforementioned embodiment, the head element includes vibration means adapted to transfer vibrations to an outer surface of the head element. So, the head element may be used to accommodate vibration means without affecting the size of the elongated body. The first coupling means may be adapted to transfer vibrations created by the vibration means to the second coupling means and, hence, to the elongated body in order to enhance the vibration effect. Moreover, a button for controlling the vibration means may be provided at an outer surface of the head element.

According to a still further modification of the aforementioned embodiment, the head element comprises illuminating means which may be located at a portion of the head element where the first coupling means is provided. The illuminating means may surround the head element and in particular its portion where the first coupling means is provided and/or the first coupling means so as to form a surrounding illuminating ring.

So, according to the aforementioned modifications, the head element may be provided for creating vibrations and/or light. However, the head element is not restricted to a vibrating and/or illuminating function, but open to whatsoever other different useful functions.

Further, the head element may include a battery and the first coupling means may include a electrical connector for connection of an electrical cable for charging the battery. So, the head element can be advantageously used for accommodation of a battery without affecting the size of the elongated body.

If the head element is provided with illuminating means and includes a battery, the illuminating means may also be used to indicate the charging condition of the battery.

According to a still further preferred embodiment, an outer surface of the elongated body is at least partly made of silicon which in particular may be a satin finished flexible silicon.

In the following, a preferred embodiment according to the present invention will be described with reference to the accompanying drawings in which.

Figure 1:
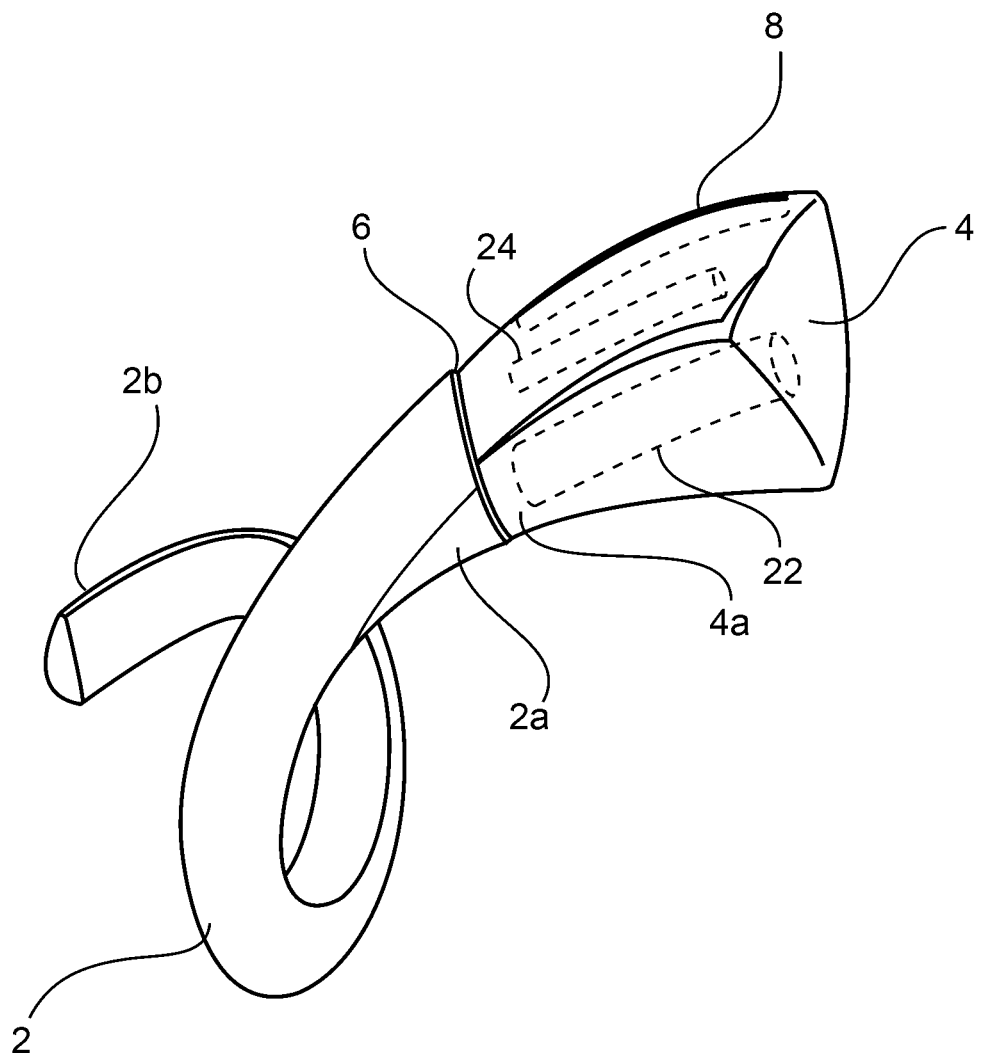
FIG. 1 is a perspective side view of a penile constriction ring according to a preferred embodiment of the present invention in a completely assembled state, wherein a vibration means and a battery accomodated within a head element are additionally shown in dotted lines.

FIG. 1 shows a penile constriction ring according to a preferred embodiment of the present invention in a completely assembled state and in an operational mode. The penile constriction ring comprises an elongated body 2 having a first end portion 2a and a second end portion 2b. In the shown embodiment, the elongated body 2 forms a strip-like element. Further, the elongated body 2 is provided with such a shape and elasticity that in the operational mode, as shown in FIG. 1, both its end portions 2a, 2b are biased into mutually overlapping positions so as to be twisted or to form at least a part of a coil or a helix. Preferably, the material of the elongated body 2 may be polyethylene and/or polypropylene, and/or the elongated body 2 is covered by a layer or a skin made of satin finished flexible silicon.

Preferably, the elongated body 2 includes an elongated elastic spring member (not shown in the figures) which creates the required biasing force so as to bias the elongated body 2 into an at least partly twisted or helical or coil-shaped form in the operational mode according to FIG. 1. Due to biasing into the operational mode, the elongated body 2 wraps itself around the organ, wherein the helix shape shown in FIG. 1 offers a tight and individually fitting shape. In order to release the penile constriction ring from the organ, both end portions 2a, 2b of the elongated body 2 are grasped and extended so as to enable the elongated body 2 to be 'unwound' against the intrinsic biasing force. However, when letting loose the end portions 2a, 2b of the elongated body 2, the elongated body 2 will return due to the biasing force from an extended shape to the helix shape in the operational mode according to FIG. 1.

As further shown in the figures, the penile constriction ring according to the described embodiment comprises a head element 4 having an end portion 4a. The head element 4 with its end portion 4a is mounted to the first end portion 2a of the elongated body as shown in FIG. 1. In the shown embodiment, the head element 4 defines an elongated piece whose shape is adapted to the shape of the elongated body 2, so that the head element 4 appears to be integral in shape with the elongated body 2.

Whereas the elongated body 2 is made of flexible or elastic material, in the described embodiment the head element 4 is made of rigid plastic material which preferably may be provided with a satin finished metal optic. As further seen from the figures, the head element 4 is provided with rounded edges and slightly convex surfaces so as to obtain a smooth appearance.

As further shown in FIG. 1, the head element 4 comprises an illuminating ring 6 which surrounds the end portion 4a of the head element along its edge.

In order to activate or deactivate vibration means to be described later in greater detail, an on/off button 8 is provided on the surface of the head element 4. Additionally or alternatively, the on/off button 8 may be provided to switch on and off the illuminating ring 6.

Figure 2:
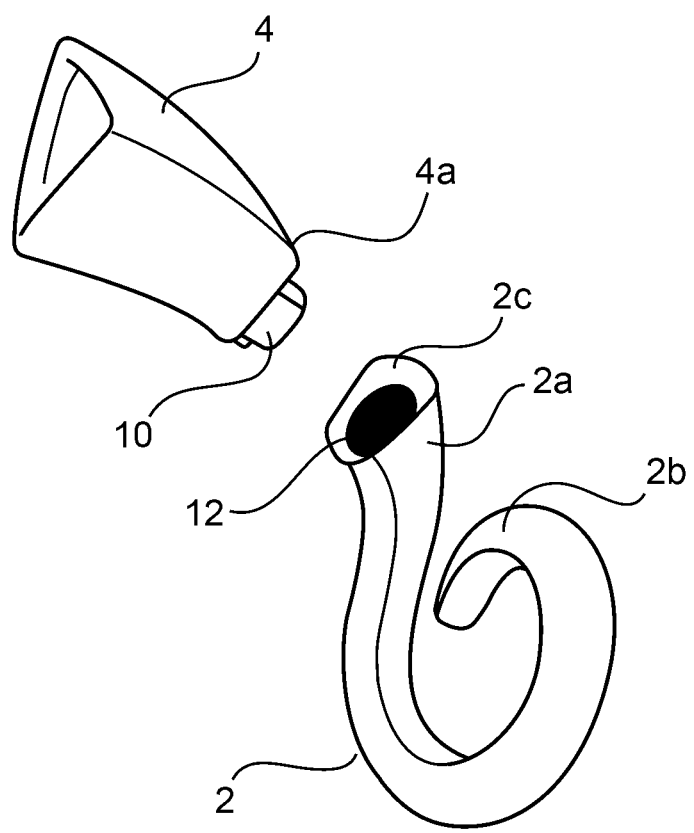
FIG. 2 is another perspective view of the penile constriction ring of FIG. 1 with its head element being separated from its elongated body.
Figure 3:
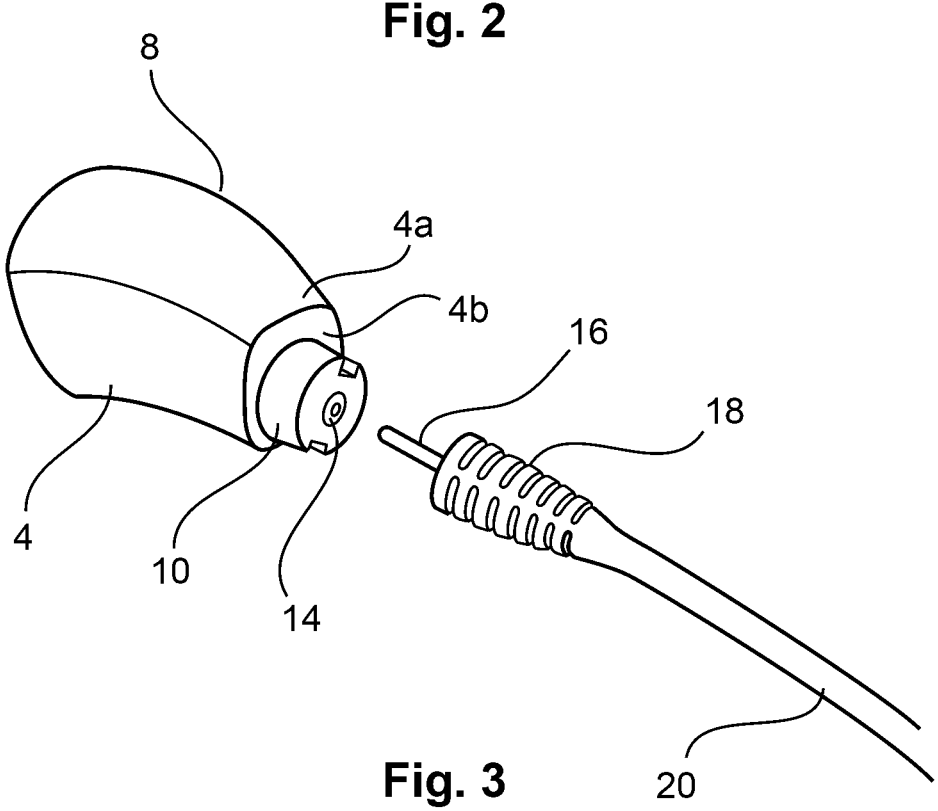
FIG. 3 is a perspective view of the head element and a cable disconnected from the head element.

FIG. 2 shows the head element 4 disconnected from the elongated body 2. So, in the described embodiment, the mounting of the head element 4 to the elongated body 2 is releasable. As shown in FIGS. 2 and 3, a male connector 10 is arranged at an end face 4d limiting the end portion 4a of the head element 4. As further shown in FIG. 2, the first end portion 2a of the elongated body 2 comprises an end face 2c including an opening 12 which is provided as female connector. The male connector 10 at the head element 4 and the opening 12 in the end face 2c of the elongated body 2 are shaped and dimensioned such that the male connector 10 of the head element 4 fits into the opening 12 of the elongated body 2. The male connector 10 and the opening 12 comprise complementary engaging portions which are adapted to provide between the head element 4 and the elongated body 2 a tight coupling which, however, is releasable. In particular, said engaging portions may comprise releasably arresting means. Further, the male connector 10 and the opening 12 are adapted to transfer vibrations created by the vibration means in the head element 4 to the elongated body 2.

As shown in FIG. 3, an electrical socket 14 is provided in the male connector 10. The socket 14 is adapted to accommodate a lug jack 16 of an electrical plug 18 coupled with a cable 20 in order to connect a battery to be described below in greater detail to an external electrical charging device (not shown) for charging the battery. FIG. 3 shows the electrical plug 18 with its cable 20 disconnected from the socket 14 at the head element 4.

As further shown by dotted lines in FIG. 1, the vibration means denoted by reference numeral "22" and the chargeable battery denoted by reference numeral "24" are arranged within the head element 4. The vibration means 22 which preferably comprises an electrical motor and an excenter rotatably driven by the motor for creating vibrations is adapted to transfer vibrations to the surface of the head element 4 as well as into the elongated body 2. The battery 24 is provided for supplying the illuminating ring 6 and the vibration means 22 with electrical power. As already mentioned above, the vibration means 22 is activated or deactivated by the on/off button 8 which is adapted to connect the vibration means 22 to the battery 24. When the battery 24 is charged due to the connection of the electrical plug 18 with the electrical socket 14, preferably the illuminating ring 6 is also used to indicate the charging condition of the battery, e.g. by emitting a flash light.

The invention claimed is:

1. A penile constriction device comprising:
an elongated body comprising a coil-shaped portion which creates a biasing force and first and second end portions, wherein each of the end portions has an overlapping section biased into a mutually overlapping position with the overlapping section of the other end portion, wherein the overlapping sections are longitudinally spaced apart in an operational mode;
wherein the coil-shaped portion has a coil shape in the operational mode and is adapted to wrap closely around a penis and to be released from the penis by unwinding the coil-shaped portion from the penis; and
wherein the coil-shaped portion is sufficiently elastic so that after being released from the penis by unwinding, the coil-shaped portion will spontaneously return to its operational mode shape due to the biasing force.

2. The device according to claim 1, wherein the coil-shaped portion of the elongated body includes an elongated elastic spring member.

3. The device according to claim 2, wherein the spring member is adapted to bias the coil-shaped portion of the elongated body into a shape of a coil.

4. The device according to claim 1, further comprising a head element removably mounted to the first end portion of the elongated body.

5. The device according to claim 4, wherein the head element includes vibration means for transferring vibrations to an outer surface of the head element.

6. The device according to claim 5 further comprising a coupling means for transferring vibrations created by the vibration means to the elongated body.

7. The device according to claim 5, wherein a button for controlling the vibration means is provided at the head element.

8. The device according to claim 5, wherein the head element includes a battery.

9. The device according to claim 8, wherein the illuminating means is adapted to indicate a charging condition of the battery.

10. The device according to claim 8 wherein the head element includes electrical coupling means for charging the battery.

11. The device according to claim 4, wherein the head element further comprises illuminating means for providing light.

12. The device according to claim 11, wherein the illuminating means is arranged at a portion of the head element.

13. The device according to claim 12, wherein the illuminating means comprises an illuminating ring.

14. The device according to claim 11, wherein the illuminating means is adapted to provide light that surrounds the head element.

15. The device according to claim 1, wherein an outer surface of the elongated body is at least partly made of silicon.

16. A penile constriction device comprising:
an elongated body comprising a first end portion, a second end portion and an intermediate coil-shaped section disposed between the first and second end portions, wherein the coil-shaped portion creates a biasing force and has overlapping curved portions;
wherein the overlapping curved portions of the coil-shaped section are longitudinally spaced apart;
wherein the coil-shaped section has elasticity and is configured:
so that, in an operational mode, it can be wrapped around a penis and has a shape to closely engage and to constrict the penis; and
so that it can be released and removed from the penis by unwinding the coil-shaped section from the penis; and
wherein the coil-shaped section is sufficiently elastic so that after being released from the penis by unwinding, the coil-shaped portion will spontaneously return to its operational mode shape due to the biasing force.

17. The device according to claim 16 further comprising a head element removably mounted to the first end portion of the elongated body.

18. The device according to claim 17 wherein the head element includes vibration means for transferring vibrations to an outer surface of the head element.

19. The device according to claim 18 further comprising a coupling means for transferring vibrations created by the vibration means to the elongated body.

* * * * *